United States Patent
Lin et al.

(10) Patent No.: US 7,600,416 B2
(45) Date of Patent: Oct. 13, 2009

(54) APPARATUS FOR MEASURING SURFACE TENSION

(75) Inventors: Li-Hua Lin, Tainan (TW); Meng-Yu Lin, No. 11, Lane 14, Sec. 2, Tung-Kuang Rd., E. Dist., Tainan City (TW); Hsiao-Jui Kuo, Tainan (TW)

(73) Assignee: Meng-Yu Lin, Tainan (TW)

( * ) Notice: Subject to any disclaimer, the term of this patent is extended or adjusted under 35 U.S.C. 154(b) by 62 days.

(21) Appl. No.: 12/031,465

(22) Filed: Feb. 14, 2008

(65) Prior Publication Data
US 2009/0205410 A1 Aug. 20, 2009

(51) Int. Cl.
*G01N 13/02* (2006.01)
(52) U.S. Cl. ............... 73/64.52; 73/64.48; 73/64.51
(58) Field of Classification Search ........... 73/64.48, 73/64.49, 64.51, 64.52
See application file for complete search history.

(56) References Cited

U.S. PATENT DOCUMENTS

| | | | | |
|---|---|---|---|---|
| 1,810,992 A * | 6/1931 | Von Dallwitz-Wegner | . | 73/54.01 |
| 2,343,061 A * | 2/1944 | Irany | ................ | 73/54.04 |
| 2,401,053 A * | 5/1946 | Cupples | ................ | 73/64.51 |
| 3,277,694 A * | 10/1966 | Cannon et al. | ............ | 73/54.07 |
| 3,520,179 A * | 7/1970 | Reed | ................ | 73/54.04 |
| 3,699,804 A * | 10/1972 | Gassmann et al. | ......... | 73/54.07 |
| 3,713,328 A * | 1/1973 | Aritomi | ................ | 73/54.08 |
| 3,720,097 A * | 3/1973 | Kron | ................ | 73/54.04 |
| 3,765,227 A * | 10/1973 | Campbell et al. | .......... | 73/64.51 |
| 3,911,728 A * | 10/1975 | Fixot | ................ | 73/54.04 |
| 4,361,032 A * | 11/1982 | Lessnig et al. | ............ | 73/64.52 |
| 4,856,322 A * | 8/1989 | Langrick et al. | ........... | 73/54.13 |
| 5,224,375 A * | 7/1993 | You et al. | ................ | 73/54.08 |
| 6,261,244 B1 * | 7/2001 | Kensey et al. | ............... | 600/573 |
| 6,322,524 B1 * | 11/2001 | Kensey et al. | ............... | 600/573 |
| 6,322,525 B1 * | 11/2001 | Kensey et al. | ............... | 600/573 |
| 6,402,703 B1 * | 6/2002 | Kensey et al. | ............... | 600/573 |
| 6,428,488 B1 * | 8/2002 | Kensey et al. | ............... | 600/573 |
| 6,450,974 B1 * | 9/2002 | Kim et al. | ................... | 600/573 |
| 6,484,565 B2 * | 11/2002 | Shin et al. | .................. | 73/54.01 |
| 6,484,566 B1 * | 11/2002 | Shin et al. | .................. | 73/54.07 |

(Continued)

FOREIGN PATENT DOCUMENTS

DE 3516406 A1 * 11/1986

(Continued)

*Primary Examiner*—David A. Rogers
(74) *Attorney, Agent, or Firm*—DLA Piper LLP (US)

(57) ABSTRACT

An apparatus for measuring surface tension includes: a U-shaped communicating tube having a base section that defines a horizontal line, and first and second sections that extend from the base section, and that respectively have first and second top open ends distal from the base section; and a capillary connected to the second top open, and having a top open end. The U-shaped communicating tube has a diameter greater than that of the capillary such that the U-shaped communicating tube does not exhibit capillary property when a liquid is filled therein. The first top open end has a height relative to the horizontal line that is greater than that of the top open end of the capillary such that the height difference therebetween is greater than that between the liquid level at the first section and a liquid drop formed on the top open end of the capillary.

9 Claims, 3 Drawing Sheets

U.S. PATENT DOCUMENTS

| | | |
|---|---|---|
| 6,745,615 B2 * | 6/2004 | Kensey et al. ............... 73/54.04 |
| 6,796,168 B1 * | 9/2004 | Goldstein et al. ........... 73/54.01 |
| 6,907,772 B2 * | 6/2005 | Kensey et al. ............... 73/54.04 |
| 7,111,499 B2 * | 9/2006 | Keen ......................... 73/54.04 |
| 2001/0039828 A1 * | 11/2001 | Shin et al. ................... 73/54.01 |
| 2002/0148281 A1 * | 10/2002 | Shin et al. ................... 73/54.01 |
| 2003/0005752 A1 * | 1/2003 | Shin et al. ................... 73/54.01 |
| 2003/0158500 A1 * | 8/2003 | Kensey et al. ............... 600/573 |

FOREIGN PATENT DOCUMENTS

| | | | |
|---|---|---|---|
| EP | 1279945 A1 | * | 1/2003 |
| JP | 62036538 A | * | 2/1987 |

* cited by examiner

APPARATUS FOR MEASURING SURFACE TENSION

BACKGROUND OF THE INVENTION

1. Field of the Invention

This invention relates to an apparatus for measuring surface tension.

2. Description of the Related Art

When a tube, which is relatively narrow and long, is inserted into a beaker filled with a liquid, it can be found that the height of the liquid in the tube is higher than that in the beaker. The phenomenon is caused by surface tension between the liquid and air. Surface tension enables a liquid to maintain a minimum surface area so that energy of the surface of the liquid is minimized and the liquid surface is maintained at a stable state.

Since a conventional apparatus for measuring surface tension is somewhat complicated and difficult to operate, there is a need in the art to provide an apparatus for measuring surface tension, that is simple and easy to operate.

SUMMARY OF THE INVENTION

According to this invention, an apparatus for measuring surface tension includes: a U-shaped communicating tube having a base section that defines a horizontal line, and first and second sections that extend from the base section, that are opposite to each other, and that respectively have first and second top open ends distal from the base section; and a capillary connected to and extending from the second top open end of the second section of the U-shaped communicating tubes in fluid communication with the U-shaped communicating tuber and having a top open end. The U-shaped communicating tube has a diameter greater than that of the capillary such that the U-shaped communicating tube does not exhibit capillary property when a liquid is filled therein. The first top open end of the first section of the U-shaped communicating tube has a height relative to the horizontal line that is greater than that of the top open end of the capillary such that the height difference therebetween is greater than that between the liquid level at the first section of the U-shaped communicating tube and a liquid drop formed on the top open end of the capillary.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
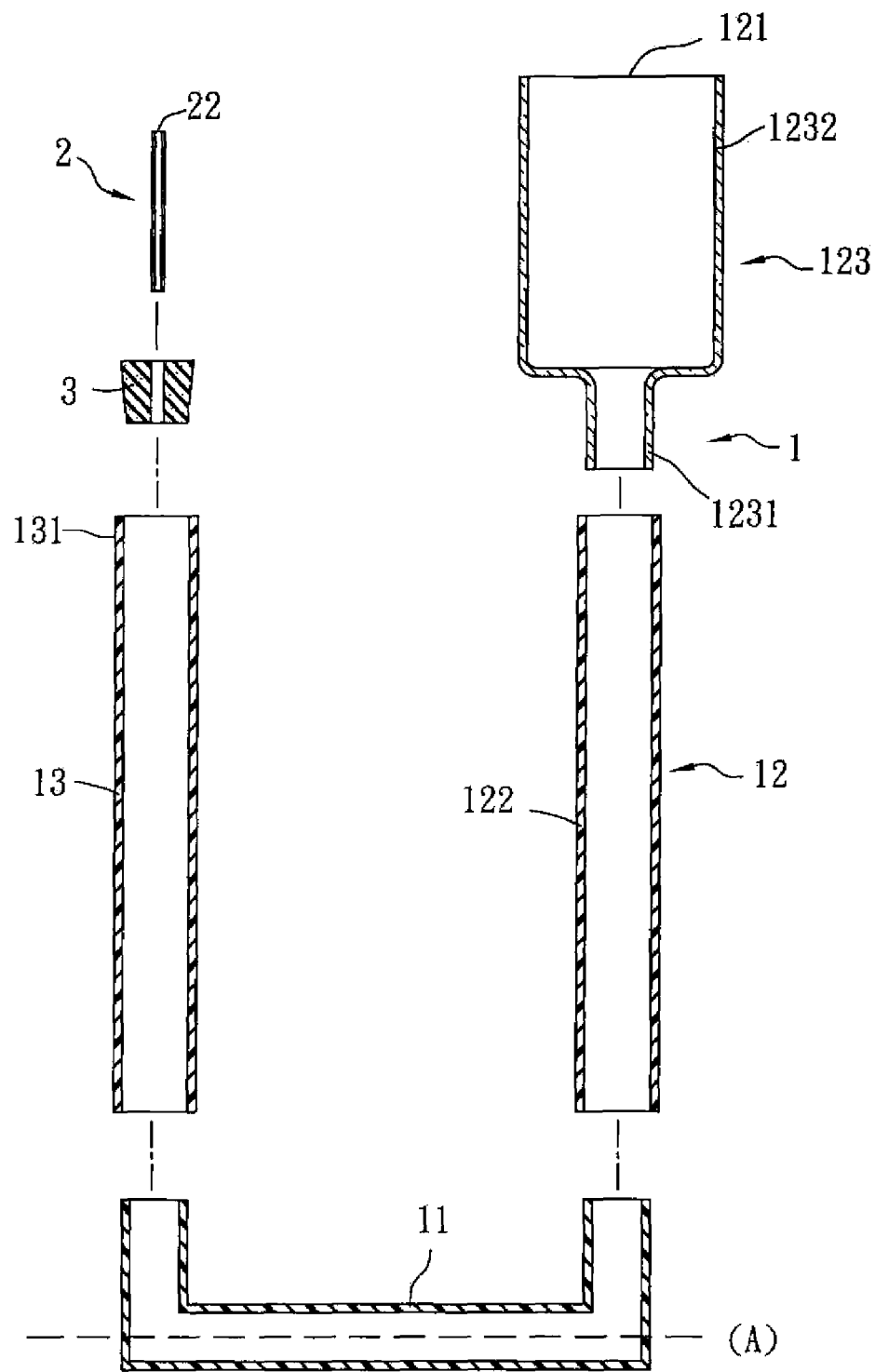
FIG. 1 is an exploded sectional view of the preferred embodiment of an apparatus for measuring surface tension according to this invention.
Figure 2:
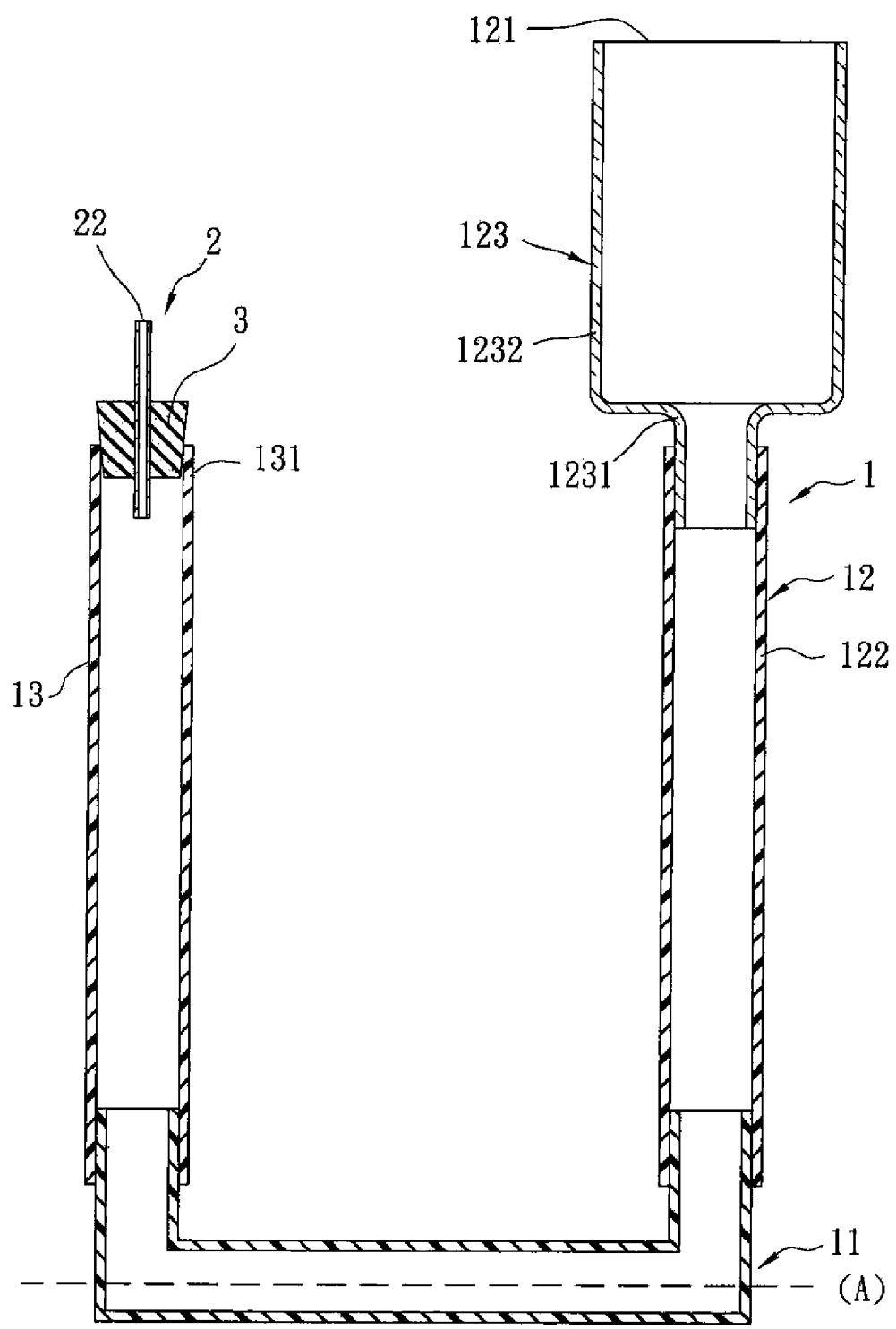
FIG. 2 is an assembled sectional view of the preferred embodiment shown in FIG. 1.

Referring to FIGS. 1 and 2, the preferred embodiment of an apparatus for measuring surface tension according to the present invention is shown to include a U-shaped communicating tube 1 and a capillary 2. The U-shaped communicating tube 1 has a base section 11 that defines a horizontal line (A), and first and second sections 12, 13 that extend from the base section 11, that are opposite to each other, and that respectively have first and second top open ends 121, 131 distal from the base section 11. The capillary 2 is connected to and extends from the second top open end 131 of the second section 13 of the U-shaped communicating tube 1, is in fluid communication with the U-shaped communicating tube 1, and has a top open end 22. The U-shaped communicating tube 1 has a diameter greater than that of the capillary 2 such that the U-shaped communicating tube 1 does not exhibit capillary property when a liquid is filled therein. The first top open end 121 of the first section 12 of the U-shaped communicating tube 1 has a height relative to the horizontal line (A) that is greater than that of the top open end 22 of the capillary 2 such that the height difference therebetween is greater than that between the liquid level at the first section 12 of the U-shaped communicating tube 1 and a liquid drop 16 formed on the top open end 22 of the capillary 2 (see FIG. 3c).

Preferably, the first section 12 of the U-shaped communicating tube 1 has a lower portion 122 and an upper portion 123. The upper portion 123 has a connecting segment 1231 that is detachably connected to the lower portion 122, and a free segment 1232 that is enlarged in cross-section from the connecting segment 1231. As shown in FIG. 2, the connecting segment 1231 of the upper portion 123 of the first section 12 is sealingly fitted into the lower portion 122 of the first section 12. Furthermore, the free segment 1232 has a diameter greater than that of the lower portion 122, and defines the first top open end 121 of the first section 12 of the U-shaped communicating tube 1. Preferably, the free segment 1232 has an inner diameter not less than 36 mm. In addition, preferably, the top open end 22 of the capillary 2 has a diameter ranging from 0.5 to 2 mm.

The apparatus further includes an elastic plug 3 that is sealingly and detachably fitted into the second top open end 131 of the second section 13 of the U-shaped communicating tube 1. The capillary 2 extends sealingly through the elastic plug 3 and into the second section 13.

It should be noted that, in the preferred embodiment of this invention, although the capillary 2 and the U-shaped communicating tube 1 are two separate parts, they can be integrally formed, and thus, the elastic plug 3 can be dispensed with. Furthermore, as shown in FIG. 1, the base section 11, the first section 12, and the second section 13 of the U-shaped communicating tube 1 are three separate parts. In other embodiments, they can be integrally made.

It should be noted that the capillary 2 can be made from any material suitable for this invention. However, since fluoropolymeric resin has minimum adsorption with respect to a liquid, the capillary 2 is preferably made from polytetrafluoroethylene so as to prevent the adsorption of the liquid at an inner surface and the top open end 22 of the capillary 2.

The measurement of surface tension using the apparatus of this invention will now be described in detail hereinbelow.

First of all, it is well known that surface tension (T) can be obtained using the following formula.

$$T = \rho g h r / 2$$

Specifically, in this invention, ρ is specific weight of the liquid; g is the acceleration due to gravity; h is height difference between the liquid levels at the upper portion 123 of the first section 12 and the top open end 22 of the capillary 2 (the height of the liquid drop 16 formed on the top open end 22 of the capillary 2 can be disregarded); and r is an inner radius of the capillary 2.

Figures 3A, 3B, 3C:
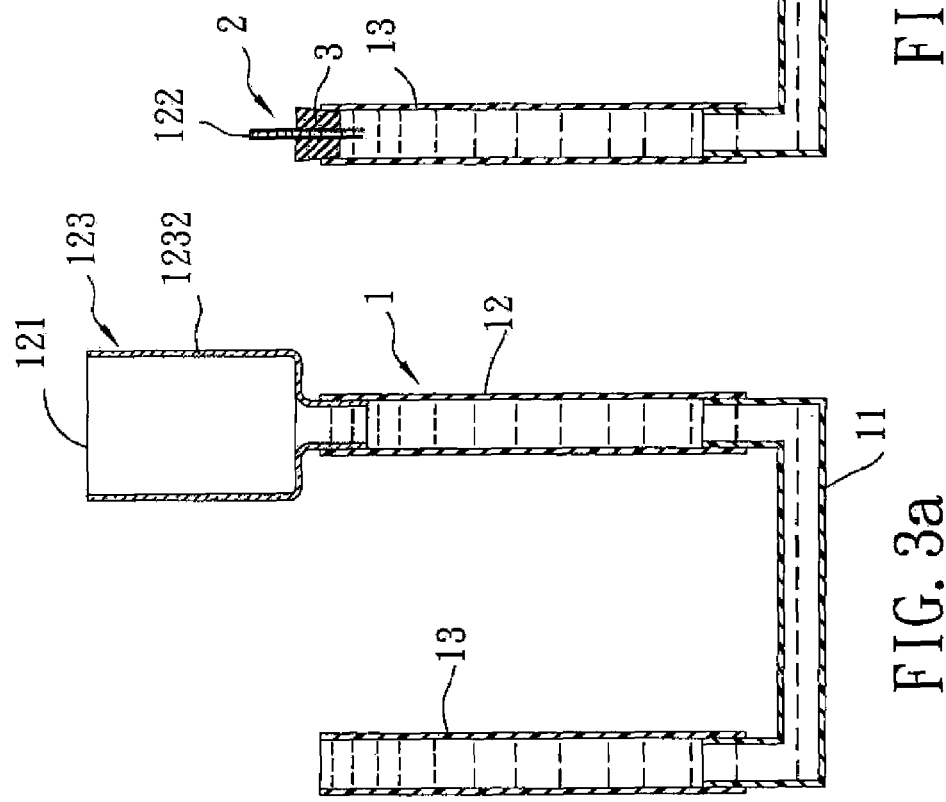
FIGS. 3a, 3b, and 3c are schematic sectional views illustrating consecutive steps for measuring surface tension using the preferred embodiment of the apparatus according to this invention.

As shown in FIG. 3*a*, after assembling the U-shaped communicating tube 1 of the apparatus shown in FIG. 1, a liquid to be tested (e.g., water, sugar solution, soybean sauce, mercury, glycerol, etc.) is poured into the apparatus through the free segment 1232 of the upper portion 123. After filling the U-shaped communicating tube 1 with the liquid, the capillary 2 is connected to the second section 13 of the U-shaped communicating tube 1 through the elastic plug 3 (see FIG. 3*b*). Then, the liquid is, again, slowly poured into the free segment 1232 of the upper portion 123 until the liquid flows out of the capillary 2. After the liquid stops flowing out of the capillary 2 (i.e., under static state), the height difference (h) between the liquid levels at the upper portion 123 of the first section 12 and the top open end 22 of the capillary 2 is measured so as to obtain the surface tension (see FIG. 3*c*).

The height difference (h) can be measured using a laser level meter. In addition, in order to easily determine the height of the liquid in the upper portion 123 of the first section 12, the upper portion 123 is preferably transparent.

In addition, the applicant conducted a series of tests to determine the influence of the length of the capillary 2 on measurement of surface tension. As shown in Table 1, the height differences (h) in groups (A) and (B) are identical. In group (C), i.e., the length of the capillary is 200 mm, the height difference (h) is increased by 0.8 mm as compared with groups (A) and (B). With respect to the height difference (h) attributed to the surface tension (i.e., 60 mm), the influence of 0.8 mm on the measurement of surface tension is small. Therefore, the length of the capillary 2 has little influence on surface tension measurement.

TABLE 1

Liquid: water
Material of the capillary: polytetrafluoroethylene
Inner diameter of the capillary: 0.5 mm
Inner diameter of the free segment: 82 mm

| | Group | | |
|---|---|---|---|
| | (A) | (B) | (C) |
| Length of the capillary (mm) | 50 | 100 | 200 |
| Height difference (h) of Exp. 1 | 61.9 | 61.4 | 62.2 |
| Height difference (h) of Exp. 2 | 61.9 | 61.9 | 62.6 |
| Height difference (h) of Exp. 3 | 61.6 | 62.2 | 63.0 |
| Average of height difference (h) | 61.8 | 61.8 | 62.6 |

In addition, as described above, the free segment 1232 preferably has an inner diameter not less than 36 mm. By choosing the inner diameter of the free segment 1232 to be not less than 36 mm, the capillary phenomenon of the free segment 1232 can be greatly decreased (see Table 2). As shown in Table 2, in groups (E) to (J) where the inner diameter of the free segment 1232 ranges from 5.0 to 26.0 mm, the height difference (h) thus measured is relatively high as compared with groups (A) to (D) where the inner diameter of the free segment 1232 is not less than 36 mm.

TABLE 2

Liquid: water
Material of the capillary: polytetrafluoroethylene
Inner diameter of the capillary: 0.5 mm
Length of the capillary: 50 mm

| | Group | | | | | | | | | |
|---|---|---|---|---|---|---|---|---|---|---|
| | (A) | (B) | (C) | (D) | (E) | (F) | (G) | (H) | (I) | (J) |
| Inner diameter of the free segment (mm) | 93.0 | 82.0 | 45.7 | 36.0 | 26.0 | 16.4 | 9.0 | 8.0 | 6.0 | 5.0 |
| Height difference (h) of Exp. 1 | 60.2 | 59.6 | 59.6 | 61.1 | 61.8 | 61.5 | 63.7 | 63.6 | 64.0 | 63.1 |
| Height difference (h) of Exp. 2 | 60.0 | 59.6 | 59.4 | 60.0 | 61.5 | 61.0 | 64.0 | 63.9 | 63.9 | 64.6 |
| Height difference (h) of Exp. 3 | 59.6 | 59.2 | 60.0 | 59.8 | 61.6 | 61.1 | 63.2 | 64.0 | 64.2 | 64.0 |
| Average of height difference (h) | 59.9 | 59.5 | 59.7 | 60.3 | 61.6 | 61.2 | 63.6 | 63.8 | 64.0 | 63.9 |

In order to prove the apparatus of this invention, several liquids (e.g. pure water, glycerol, olive oil, and alcohol) are used for testing the accuracy of the apparatus in measuring surface tension. The tests are measured at 20° C. As shown in Table 3, the value of surface tension measured using the apparatus of this invention is very close to the standard surface tension (obtained from the published information on the internet) for each test liquid. (請確認本段敘述是否ok)

TABLE 3

| Liquid | Standard surface tension (dyne/cm) | Surface tension measured using the apparatus of this invention (dyne/cm) |
| --- | --- | --- |
| Pure water | 72.8 | 72.5 |
| Glycerol | 63.1 | 63.4 |
| Olive oil | 32.0 | 31.0 |
| Alcohol | 22.3 | 22.9 |

In order to prove the apparatus of this invention, several liquids (e.g. pure water, glycerol, olive oil, and alcohol) are used for testing the accuracy of the apparatus in measuring surface tension. The tests are measured at 20° C. As shown in Table 3, the value of surface tension measured using the apparatus of this invention is very close to the standard surface tension (obtained from the published information on the internet) for each test liquid.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. An apparatus for measuring surface tension, comprising:
   a U-shaped communicating tube having a base section that defines a horizontal line, and first and second sections that extend from said base section, that are opposite to each other, and that respectively have first and second top open ends distal from said base section; and
   a capillary connected to and extending from said second top open end of said second section of said U-shaped communicating tube, in fluid communication with said U-shaped communicating tube, and having a top open end;
   wherein said U-shaped communicating tube has a diameter greater than that of said capillary such that said U-shaped communicating tube does not exhibit capillary property when a liquid is filled therein;
   wherein said first top open end of said first section of said U-shaped communicating tube has a height relative to said horizontal line that is greater than that of said top open end of said capillary such that the height difference therebetween is greater than that between the liquid level at said first section of said U-shaped communicating tube and a liquid drop formed on said top open end of said capillary.

2. The apparatus of claim 1, wherein said top open end of said capillary has a diameter ranging from 0.5 to 2 mm.

3. The apparatus of claim 1, further comprising an elastic plug that is sealingly and detachably fitted into said second top open end of said second section of said U-shaped communicating tube, said capillary extending sealingly through said elastic plug and into said second section.

4. The apparatus of claim 1, wherein said capillary is made from a fluoropolymeric resin.

5. The apparatus of claim 4, wherein said fluoropolymeric resin is polytetrafluoroethylene.

6. The apparatus of claim 1, wherein said first section of said U-shaped communicating tube has a lower portion and an upper portion having a connecting segment that is detachably connected to said lower portion, and a free segment that is enlarged in cross-section from said connecting segment, that has a diameter greater than that of said lower portion, and that defines said first top open end of said first section of said U-shaped communicating tube.

7. The apparatus of claim 6, wherein said connecting segment of said upper portion of said first section of said U-shaped communicating tube is sealingly fitted into said lower portion of said first section.

8. The apparatus of claim 6, wherein said free segment of said upper portion of said first section of said U-shaped communicating has a diameter not less than 36 mm.

9. The apparatus of claim 6, wherein said free segment of said upper portion of said first section of said U-shaped communicating is transparent.

* * * * *